US005849727A

United States Patent [19]

Porter et al.

[11] Patent Number: 5,849,727

[45] Date of Patent: Dec. 15, 1998

[54] COMPOSITIONS AND METHODS FOR ALTERING THE BIODISTRIBUTION OF BIOLOGICAL AGENTS

[75] Inventors: Thomas R. Porter; Patrick L. Iversen, both of Omaha, Nebr.

[73] Assignee: Board of Regents of the University of Nebraska, Lincoln, Nebr.

[21] Appl. No.: 670,999

[22] Filed: Jun. 28, 1996

[51] Int. Cl.$^6$ .................. A01N 51/00

[52] U.S. Cl. .................. 514/156; 514/210; 514/226.2; 514/359; 514/376; 514/460; 514/471; 514/569; 514/577; 514/724; 514/776

[58] Field of Search .................. 514/44, 156, 210, 514/226.2, 359, 396, 460, 471, 569, 577, 724, 776; 424/94.3

[56] References Cited

U.S. PATENT DOCUMENTS

| | | | |
|---|---|---|---|
| 4,572,203 | 2/1986 | Feinstein | 424/9.52 |
| 4,634,586 | 1/1987 | Goodwin et al. | 424/1.1 |
| 4,718,433 | 1/1988 | Feinstein | 424/9.52 |
| 4,774,958 | 10/1988 | Feinstein | 424/9.52 |
| 4,844,882 | 7/1989 | Widder et al. | 424/9.52 |
| 4,957,656 | 9/1990 | Cerny et al. | 252/311 |
| 5,040,537 | 8/1991 | Katakura | 600/431 |
| 5,107,842 | 4/1992 | Levene et al. | 424/9.5 |
| 5,255,683 | 10/1993 | Monaghan | 600/958 |
| 5,304,325 | 4/1994 | Kaufman et al. | 252/312 |
| 5,310,540 | 5/1994 | Giddey et al. | 424/9.52 |
| 5,315,997 | 5/1994 | Widder et al. | 600/920 |
| 5,315,998 | 5/1994 | Tachibana et al. | 601/2 |
| 5,385,147 | 1/1995 | Anderson et al. | 600/458 |
| 5,385,725 | 1/1995 | Lin et al. | 424/9.52 |
| 5,393,524 | 2/1995 | Quay | 424/9.52 |
| 5,401,493 | 3/1995 | Lohrmann et al. | 424/9.54 |
| 5,409,688 | 4/1995 | Quay | 424/9.52 |
| 5,410,516 | 4/1995 | Uhlendorf et al. | 367/7 |
| 5,413,774 | 5/1995 | Schneider et al. | 424/9.51 |
| 5,439,686 | 8/1995 | Desai et al. | 424/451 |
| 5,445,813 | 8/1995 | Schneider et al. | 424/9.51 |
| 5,512,268 | 4/1996 | Grinstaff et al. | 424/9.322 |
| 5,540,909 | 7/1996 | Schutt | 424/9.52 |
| 5,542,935 | 8/1996 | Unger et al. | 604/190 |
| 5,552,133 | 9/1996 | Lambert et al. | 424/9.52 |
| 5,558,853 | 9/1996 | Quay | 424/9.5 |
| 5,560,364 | 10/1996 | Porter | 660/458 |
| 5,567,415 | 10/1996 | Porter | 424/9.52 |
| 5,580,859 | 12/1996 | Felgner et al. | 514/44 |

FOREIGN PATENT DOCUMENTS

| | | | |
|---|---|---|---|
| 0633 030 A1 | 1/1985 | European Pat. Off. | A61K 49/00 |
| WO 92/05806 | 3/1992 | WIPO | A61K 49/00 |
| WO 93/05819 | 4/1993 | WIPO | A61K 49/00 |
| WO 94/16739 | 8/1994 | WIPO | A61K 49/00 |
| WO 94/18954 | 9/1994 | WIPO | A61K 9/48 |
| WO 94/28874 | 12/1994 | WIPO | A61K 9/127 |
| WO 95/15118 | 6/1995 | WIPO | A61B 8/00 |
| WO 95/23615 | 9/1995 | WIPO | A61K 49/00 |
| WO 96/38180 | 12/1996 | WIPO | A61K 49/00 |
| WO 96/38181 | 12/1996 | WIPO | A61K 49/00 |
| WO 97/33474 | 9/1997 | WIPO | A61B 8/00 |

OTHER PUBLICATIONS

Porter, et al., "Interaction of Diagnostic Ultrasound with Synthetic Oligonucleotide–Labeled Perfluorocarbon–Exposed Sonicated Dextrose Albumin Microbubbles", *J Ultrasound Med*, 15:577–584 (1996).

Orkin, et al., Dec. 1995, Report and Recommendations of the Panet to Assess the NIH Investment in Research on Gene Therapy.

Gura, T, 1995, Science, vol. 270, pp. 575–577.

Bleeker, H., "On the Application of Ultrasonic Contrast Agents for Blood Flowmetry and Assessment of Cardiac Perfusion", *Ultrasound Med*, 9:461–471 (1990).

Putterman, S., "Sonoluminescene: Sound into Light", Feb. 1995, *Scientific American*, 46–51.

Porter, T., "Myocardial Contrast Echocardiography for the Assessment of Coronary Blood Flow Reserve: Validation in Humans", *JACC*, 21(2) 349–355 (1993).

Xie, F., "Acute Myocardial Ischemia and Reperfusion can be Visually Identified Non–invasively with Intravenous Perfluoropropane–Enhanced Sonicated Dextrose Albumin Ultrasound Contrast", *Abstract From the 67th Scientific Sessions Dallas Convention Center, Dallas TX, Nov. 14–17, 1994* 90(2) Part 2, Oct. 1994 (abstract).

Porter, T., "Echocardiographic Detection of Residual Coronary Flow Abnormalities and Stenosis Severity After Coronary Reperfusion Using Intravenous Perfluoropropane–enhanced Sonicated Dextrose Albumin", *J. Am. Col. of Card.*, special issue, Feb. 1995 (abstract).

Kricsfeld, A., "Detection of Regional Perfusion Abnormalities During Adenoosine Stress Echocardiography Using Intravenous Perfluoropropane–enhanced Sonicated Dextrose Albumin", *J. Am. Col. of Card.*, special issue, Feb. 1995 (abstract).

Porter, T., "Multifold Sonicated Dilutions of Albumin With Fifty Percent Dextrose Improve Left Ventricular Contrast Videointensity After Intravenous Injection in Human Beings", *J. Am. Soc. Echocard.*, 7(5) 465–471 (1994).

(List continued on next page.)

*Primary Examiner*—James Ketter
*Assistant Examiner*—Irem Yucel
*Attorney, Agent, or Firm*—Zarley, McKee, Thomte, Voorhees, & Sease

[57] ABSTRACT

This invention relates to a new and improved pharmaceutical composition and method for delivery of therapeutic or bioactive agents. The methods and composition of the invention can be used with several therapeutic or bioactive agents and can achieve site-specific delivery of a therapeutic or biologically-active substance. This can allow for lower doses and for improved efficacy with drugs, particularly agents such as oligonucleotides which are plagued with problems in achieving therapeutic levels at targeted sites.

14 Claims, 1 Drawing Sheet

OTHER PUBLICATIONS

Xie, F., "Perfluoropropane Enhanced Sonicated Dextrose Albumin Produces Visually Apparent Consistent Myocardial Opecification with Physiologic Washout and Minimal Homodynamic Changes Following. . . Injection", *Abstract From the 67th Scientific Sessions Dallas Convention Center, Dallas TX, Nov. 14–17, 1994* 90(4) Part 2, Oct. 1994 (abstract).

Porter, T., "Visually Discernible Myocardial Echocardiographic Contrast After Intravenous Injection of Sonicated Dextrose Albumin Microbubbles Containing Molecular Weight, Less Soluble Gases", *J. Am. Col. of Card.*, 25(2) 509–515 (1995).

Porter, T., "Noninvasive Indentification of Acute Myocardial Ischemia and Reperfusion with Contrast Ultrasound Using Intravenous Perfluoropropane–Exposed Sonicated Dextrose Albumin", *J. Am. Col. of Card.*, 26(1) 33–40 (1995).

Anderson editorial "Gene Therapy for Genetic Diseases", *Human Gene Therapy*, 5:281–282 (1994).

Challita, P., "Lack of expression from a retroviral vector after transduction of murine hematopoietic stem cells is associated with methylation in vivo", *Proc. Natl. Acad. Sci. USA*, 91, 2567–2571.

Jaroff, "Keys to the Kingdom", *Time*, 148(14) 24–29, Fall 1996.

Porter, "Transient Myocardial Contrast After Initial Exposure to Diagnostic Ultrasound Pressures With Minute Doses of Intravenously Injected Microbubbles; Demonstration and Potential Mechanisms", *Circulation*, 92(9):2391–2395 (1995).

Coghlan, "Gene dream fades away", *New Scientist*, 148:14–15 (1995).

Brown, "New Media, Researchers" Oversold Gene Therapy, Advisory Panel Says, *The Washington Post*, p. A22 (1995).

Marshall, "Gene Therapy's Growing Pains", *Science*, 269:1050–1055 (1995).

Porter, "The mechanism and clinical implication of improved left ventricular videointensity following intravenous injection of multi–fold dilutions of albumin with dextrose", *International J. of Card. Imag.*, 11:117–125 (1995).

Srinivasan, Shashi Kumar "Characterization of Binding Sites, Extent of Binding, and Drug Interactions of Oligonucleotides with Albumin", Antisense Research and Development 5:131–139 (1995).

Applied Pharmacokinetics, Principles of Therapeutic Drug Monitoring, Third Edition (1992), Applied Therapeutics, Inc., Vancouver, WA.

COMPOSITIONS AND METHODS FOR ALTERING THE BIODISTRIBUTION OF BIOLOGICAL AGENTS

FIELD OF THE INVENTION

This invention relates to a new and improved pharmaceutical composition and method for delivery of bioactive substances. The methods and composition of the invention can be used with several agents and can achieve site specific delivery of a biologically active substances. This can allow for lower doses and for improved efficacy with drugs particularly agents such as oligonucleotides which are plagued with problems in achieving therapeutic concentrations at targeted organs.

BACKGROUND OF THE INVENTION

Drug delivery techniques are employed in the formulation of all drug therapy to augment drug availability, to reduce drug dose, and consequently to reduce drug-induced side effects. These techniques serve to control, regulate, and target the release of drugs in the body. The goals have been to provide less frequent drug administration, to maintain constant and continuous therapeutic levels of a drug in the systemic circulation or at a specific target organ site, to achieve a reduction in undesirable side effects, and to promote a reduction in the amount and dose concentration required to realize the desired therapeutic benefit.

To date, drug delivery systems have included drug carriers based upon proteins, polysaccharides, synthetic polymers, erythrocytes, DNA and liposomes. New generation biologicals such as monoclonal antibodies, gene therapy vectors, anti-cancer drugs such as Taxol, viral based drugs, and oligo and poly nucleotides have presented several problems with regard to delivery. In fact drug delivery may be the primary hurdle to achieving mainstream therapeutic use of these biologics whose initial potential seemed unlimited but whose therapeutic parameters have prevented realization of full benefit.

Synthetic oligodeoxyribonucleotides which are chemically modified to confer nuclease resistance represent a fundamentally different approach to drug therapy. The most common applications to date are antisense oligos with sequences complementary to a specific targeted mRNA sequence. An antisense oligonucleotide approach to therapy involves a remarkably simple and specific drug design concept in which the oligo causes a mechanistic intervention in the processes of translation or an earlier processing event. The advantage of this approach is the potential for gene-specific actions which should be reflected in a relatively low dose and minimal non-targeted side effects.

Phosphorothioate analogs of polynucleotides have chiral internucleoside linkages in which one of the non-bridging ligands is sulfur. The phosphorothioate analog is currently the most commonly employed analogue in biological studies including both in vitro and in vivo. The most apparent disadvantage of phosphorothioate oligonucleotides include the high cost of preparation of sufficient amounts of high quality material and non-specific binding to proteins. Hence, the primary advantage of antisense approach (low dose and minimal side effects) fall short of expectations.

Drug delivery efforts with regard to oligonucleotides and polynucleotides have focused on two key challenges; transfection of oligonucleotides into cells and alteration of distribution of oligonucleotides in vivo.

Transfection involves the enhancement of in vitro cellular uptake. Biological approaches to improve uptake have included viral vectors such as reconstituted viruses and pseudo virions, and chemicals such as liposomes. Methods to improve biodistribution have focused on such things as cationic lipids, which are postulated to increase cellular uptake of drugs due to the positively charged lipid attraction to the negatively charged surfaces of most cells.

Lipofection and DC-cholesterol liposomes have been reported to enhance gene transfer into vascular cells in vivo when administered by catheter. Cationic lipid DNA complexes have also been reported to result in effective gene transfer into mouse lungs after intratracheal administration.

Cationic liposomal delivery of oligonucleotides has also been accomplished however, altered distribution to the lung and liver was experienced. Asialoglycoprotein poly(L)-lysine complexes have met with limited success as well as complexation with Sendai virus coat protein containing liposomes. Toxicity and biodistribution, however, have remained significant issues.

From the foregoing it can be seen that a targeted drug delivery system for delivery of biologics, particularly poly and oligo nucleotides is needed for these drugs to achieve their fullest potential.

One object of this invention is to provide a novel composition of matter to deliver a pharmaceutical agent to a targeted site in vivo.

Another object of the invention is to provide a method for delivering a pharmaceutical agent increasing drug bioavailability and decreasing toxicity.

Other objects of the inventions will become apparent from the description of the invention which follows.

SUMMARY OF THE INVENTION

According to the invention a new biologically active agent delivery method and composition are disclosed. The compositions and methods can be used to deliver agents such as therapeutics or diagnostics which have been plagued with delivery problems such as oligonucleotides as well as traditional agents and can drastically reduce the effective dosages of each, increasing the therapeutic index and improving bioavailability. This in turn can reduce drug cytotoxicity and side effects.

The invention employs conjugation of the biologic agent with a filmogenic protein which is formed as a protein shell microbubble encapsulating an insoluble gas. The composition is prepared as an aqueous suspension of a plurality of the microbubbles for parenteral administration. Conjugation of the biologic with albumin or other such protein encapsulated microbubbles can allow for targeted delivery of the biologic to alternate including those which traditionally interact with the protein.

DETAILED DESCRIPTION OF THE INVENTION

Figure 1:
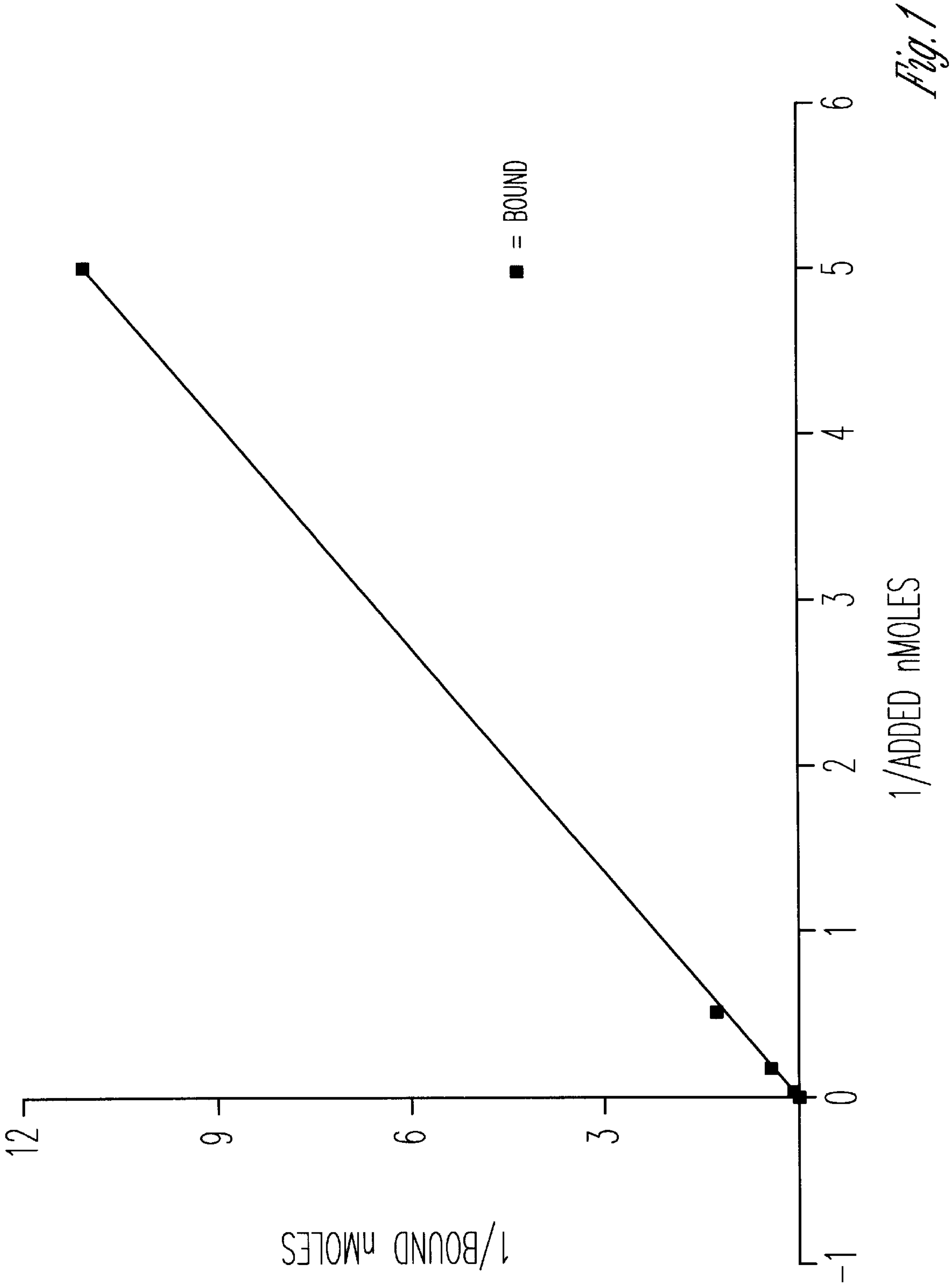
FIG. 1 is a Lineweaver-Burke plot of the binding data for PESDA microbubbles with PS-ODN. The equilibrium dissociation constant $K_m$ (calculated for the 7 concentrations which were run in duplicate) for the binding to the microbubbles was $1.76\times10^{-5}$M. ($r^2$=0.999; Y-int=0.0566; 7 concentrations). This is nearly within the range observed for binding a 15mer PS-ODN with sequence 5'd (AACGTTGAGGGGCAT)-3' (SEQ ID NO:1) to human serum albumin in solution of 3.7–4.8×10–5M previously reported Srinivasan SK et al, "Characterization of binding sites, extent of binding, and drug interactions of oligonucleotides with albumin". Antisen Res. Dev. 5:131, 1995.

Ultrasonic imaging has long been used as a diagnostic tool to aid in therapeutic procedures. It is based on the principle that waves of sound energy can be focused upon an area of interest and reflected to produce an image. Generally an ultrasonic transducer is placed on a body surface overlying the area to be imaged and ultrasonic energy, produced by generating and receiving sound waves, is transmitted. The ultrasonic energy is reflected back to the transducer where it is translated into an ultrasonic image. The amount of characteristics of the reflected energy depend upon the acoustic properties of the tissues, and contrast agents which are echogenic are preferably used to create ultrasonic energy in the area of interest and improve the imaging received. For a discussion of contrast echographic instrumentation, see, DeJong and, "Acoustic Properties of Ultrasound Contrast Agents", CIP-GEGEVENS KONINKLIJKE BIBLIOTHEEK, DENHAG (1993), pp. 120 et seq.

Contrast echocardiography has been used to delineate intracardiac structures, assess valvular competence, and demonstrate intracardiac shunts. Myocardial contrast echocardiography (MCE) has been used to measure coronary blood flow reserve in humans. MCE has been found to be a safe and useful technique for evaluating relative changes in myocardial perfusion and delineating areas at risk.

Ultrasonic vibration has also been used at therapeutic levels in the medical field to increase the absorption of various medicaments. For example in Japanese Patent Kokai number 115591/1977 discloses that percutaneous absorption of a medicament is enhanced by ultrasonic vibration. U.S. Pat. Nos. 4,953,565 and 5,007,438 also disclose a technique of percutaneous absorption of medicaments by the aid of ultrasonic vibration. U.S. Pat. No. 5,315,998 discloses a booster for drug therapy comprising microbubbles in combination ultrasonic energy to allow the medicament to diffuse and penetrate. This discloses the use of therapeutic levels of ultrasound for up to 20 minutes in contrast to the invention which uses diagnostic levels of ultrasound with exposure for much shorter time periods to achieve release of conjugated bioactive agents.

Applicant has demonstrated that traditional diagnostic ultrasound therapy contrast agents can be used as a specific targeted delivery device to release therapeutic agents at the specifically designated sites of interest thereby altering drug distribution. Surprisingly, this objective can be accomplished with the contrast agent alone and without the use of any diagnostic ultrasound.

The pharmaceutical composition of the invention comprises a liquid suspension containing microbubbles of an insoluble gas having a diameter of 0.1 to 10 microns. The microbubbles are formed by entrapping microbubbles of a gas into a liquid. The microbubbles are made of various insoluble gases such as fluorocarbon or sulfur hexafluoride gas. The liquid includes any liquid which can form microbubbles. Generally any insoluble gas can be used. It must be gaseous at body temperature and be nontoxic. The gas must also form stable microbubbles of average size of between about 0.1 and 10 microns in diameter when the pharmaceutical composition is sonicated to form microbubbles. Generally perfluorocarbon gases such as perfluoromethane, perfluoroethane, perfluoropropane, perfluorobutane, perfluoropentane are preferred. Of these gases, perfluoropropane and perfluorobutane are especially preferred because of their demonstrated safety for intraocular injection in humans. They have been used in human studies for intraocular injections to stabilize retinal detachments (Wong and Thompson, Opthamology 95:609–613). Treatment with intraocular perfluoropropane is considered to be the standard of care for treatment of this disorder. The gases must also have a diffusion coefficient and blood solubility lower than nitrogen or oxygen which diffuse once in the internal atmosphere of the blood vessel.

Other inert gases such as sulfur hexafluoride are also useful in the invention provided they have a diffusion coefficient and blood solubility lower than nitrogen or oxygen. The agent of the invention is formulated in a pharmaceutically effective dosage form for peripheral administration to the host. Generally such host is a human host, although other mammalian hosts such as canine or equine can also be subject to this therapy.

The pharmaceutical liquid composition of the invention uses a liquid wherein the microbubbles are stabilized by a filmogenic protein coating. Suitable proteins include naturally occurring proteins such as albumin, human gamma globulin, human apotransferin, Beta lactose and urease. The invention preferably employs a naturally occurring protein but synthetic proteins may also be used. Preferred is human serum albumin.

It is also optional to use an aqueous solution containing a mixture of a pharmaceutically accepted saccharide e.g., dextrose, in combination with the earlier described protein. In a preferred embodiment the pharmaceutical liquid composition of the invention is the sonicated mixture of commercially available albumin (human), U.S.P. solution (generally supplied as 5% or 25% by weight sterile aqueous solutions), and commercially available dextrose, U.S.P. for intravenous administration. The mixture is sonicated under ambient conditions i.e. room air temperature and pressure and is perfused with an insoluble gas (99.9% by weight) during sonication.

In a most preferred embodiment the pharmaceutical liquid composition includes a two-fold to eight-fold dilution of 5% to 50% by weight of dextrose and a 2% to 10% by weight of human serum albumin. Exemplary of other saccharide solutions of the invention are aqueous monosaccharide solution (e.g. having the formula $C_6H_{12}O_6$ such as the hexose sugars, dextrose or fructose or mixtures thereof), aqueous disaccharide solution (e.g. having a formula $C_{12}H_{22}O_{11}$ such as sucrose, lactose or maltose or mixtures thereof), or aqueous polysaccharide solution (e.g. soluble starches having the formula $C_6H_{10}O_5(n)$ wherein n is a whole number integer between 20 and about 200 such as amylase or dextran or mixtures thereof.

The microbubbles are formed by sonication, typically with a sonicating horn. Sonication by ultrasonic energy causes cavitation within the dextrose albumin solution at sites of particulate matter or gas in the fluid. These cavitation sites eventually resonate and produce small microbubbles (about 7 microns in size) which are non-collapsing and stable. In general, sonication conditions which produce concentrations of greater than about $4\times10^8$m of between about 5 and about 6 micron microbubbles are preferred. Generally the mixture will be sonicated for about 80 seconds, while being perfused with an insoluble gas.

A second method of preparation includes hand agitating 15±2 ml of sonicated dextrose albumin with 8±2 ml of perfluorocarbon gas prior to sonication. Sonication then proceeds for 80±5 seconds.

These microbubble sizes are particularly ideal since a microbubble must have a mean diameter of less than 10 microns and greater than 0.1 to be sufficient for transpulmonary passage, and must be stable enough to prevent significant diffusion of gases within the microbubble following intravenous injection and during transit to the target site.

The microbubbles are next incubated with the medicament so that the medicament becomes conjugated with the microbubble. Quite unexpectedly it was demonstrated that filmogenic proteins in the form of microbubbles as previously used in contrast agents retain their ability to bind medicaments. This is surprising because traditionally it was thought that in the formation of microbubble contrast agents the protein sphere was made of denatured protein. Applicant has demonstrated that when an insoluble gas instead of air is used for the microbubble, much of the sonication energy is absorbed by the gas and the protein retains its binding activity. Air filled microbubbles do not retain their binding capabilities and cannot be used in the method of the invention.

The therapy involves the use of a pharmaceutical composition conjugated to a protein microbubble of a diameter of about 0.1 to 10 microns. The invention uses agents traditionally used in diagnostic ultrasound imaging.

Therapeutic agents useful in the present invention are selected via their ability to bind with the filmogenic protein. For example if the filmogenic protein is albumin, the therapeutic or diagnostic agent can include oligonucleotides (such as antisense or antigen oligos), polynucleotides (such as retroviral, adenoviral, plasmid vectors or probes), or ribozymes all of which can bind with albumin and as such can form a conjugation with the microbubble. A list of drugs which bind to albumin at site 1 (which retains its binding capacity) and thus would be useful in the methods and compositions of the present invention in the albumin embodiment follows:

| Drug | % Albumin | Binding Drug Class |
|---|---|---|
| Naproxen | 99.7 | NSAID⊕ |
| Piroxicam | 99.3 | NSAID⊕ |
| Warfarin | 99.0 | Anticoagulant |
| Furosemide | 98.8 | Loop diuretic |
| Phenylbutazone | 96.1 | NSAID⊕ |
| Valproic Acid | 93.0 | Antiepileptic |
| Sulfisoxazole | 91.4 | Sufonimide Antibiotic |
| Ceftriaxone | 90–95* | Third Generation cephalosporin antibiotic |
| Miconazole | 90.7–93.1* | Antifungal |
| Phenytoin | 89.0 | Antiepileptic |

⊕Nonsteroidal anti inflammatory drug
*Represents patient-to-patient variability

Other drugs which bind with albumin particularly at site 1 would also be useful in this embodiment and can be ascertained by those of skill in the art through Drug Interaction and Pharmacology tests standard to those of skill in the art such as "Drug Information" or "Facts and Comparisons" published by Berney Olin updated every quarter. Other such references are widely available in the are. Assays for determination of appropriate protein-therapeutic combinations are disclosed herein and can be sued to test any combination for its ability to work with the method of the invention.

According to a preferred embodiment of the invention, protein coated microbubbles of insoluble gas have been found to form stable conjugates with oligonucleotides. The oligo conjugated bubbles are then introduced to the animal and the protein coating directs the conjugated agent to sites of interaction. Ultimately as the bubble dissipates the agent will be released at the tissue site.

This is of particular relevance to oligonucleotide and polynucleotide therapy as the primary hurdle to effective anti-sense, anti-gene, or even gene therapy employing viral or plasmid nucleotide delivery is the ability of the therapeutic to reach the target site at high enough concentrations to achieve a therapeutic effect. Therapeutic sites can include such things as the location of a specific tumor, an organ which due to differential gene activation expresses a particular gene product, the site of an injury or thrombosis, a site for further processing and distribution of the therapeutic etc. Generally the target site is selected based upon the bioprocessing of the filmogenic protein. For example the kidneys and liver take up albumin and albumin microbubbles can be used to specifically direct the administration of conjugated bioactive agents to these areas. The metabolism and bioprocessing of other filmogenic proteins can be easily obtained through standard pharmacologic texts such as Basic and Clinical Pharmacology by Bertram G. Katzung the relevant disclosure of which is incorporated by reference.

The method preferred for practicing the delivery therapy of the invention involves obtaining a pharmaceutical liquid agent of the invention, introducing said agent into a host by intravenous injection, intravenously (i.v. infusion), percutaneously or intramuscularly. The microbubble is then processed in the animal and is taken up and interacted with according to the filmogenic protein which coats the microbubble. Ultimately the bubble dissipates delivering the bioactive at the site of processing of the protein.

It has been previously shown by applicants that microbubble conjugation of bioactive agents can be used in targeted delivery protocols with delivery of the biologic upon application of ultrasound to the target site, causing cavitation of the microbubble and ultimate release of the biologic at the site in interaction with the ultrasound field. Quite unexpectedly, applicant has now discovered that application of ultrasound is not necessary for the targeted delivery of biologics to sites of bioprocessing of the protein coating. The protein traffics the microbubble and conjugate to sites of processing and as the bubbles dissipate the oligo or other biologic is released to interact with the site allowing for a fraction of the biologic to achieve the same biological effect.

In a preferred embodiment the agent of the invention is a perfluorocarbon enhanced sonicated dextrose albumin solution comprised of a sonicated three-fold dilution of 5% human serum albumin with 5% dextrose. During sonication, the solution is perfused with perfluorocarbon gas for about 80 seconds which lowers the solubility and diffusivity of the microbubble gas. The resulting microbubbles are concentrated at room temperature for at least about 120±5 minutes wherein the excess solution settles in the sonicating syringe. The microbubbles are then exposed to a therapeutic agent and allowed to interact such that the agent becomes conjugated to the microbubbles. Next the conjugated microbubbles are transferred to a sterile syringe and injected parenterally into a mammal, preferably near the target site of activity of the agent.

Methods of ultrasonic imaging in which microbubbles formed by sonicating an aqueous protein solution are injected into a mammal to alter the acoustic properties of a predetermined area which is then ultrasonically scanned to obtain an image for use in medical procedures is well known. For example see U.S. Pat. No. 4,572,203, U.S. Pat. No. 4,718,433 and U.S. Pat. No. 4,774,958, the contents of each of which are incorporated herein by reference.

It is the use of these types of contrast agents as a pharmaceutical composition as part of a targeted delivery system that is the novel improvement of this invention.

The invention has been shown to drastically improve the efficiency and therapeutic activity by altering biodistribution of several drugs including, most notably, anti-sense oligonucleotides which have been traditionally plagued with ineffective pharmacologic parameters, including high clearance rate and toxicity.

This is particularly significant as the microbubble-therapeutic agent therapy can reduce any toxic effects of persons who perhaps could not tolerate certain therapeutics at doses and concentrations necessary to achieve a beneficial result.

The protein substance such as human serum albumin is easily metabolized within the body and excreted outside and hence is not harmful to the human body. Further gas trapped within the microbubbles is extremely small and is easily dissolved in blood fluid, perfluoropropane and perfluorobutane have long been known to be safe in humans. Both have been used in humans for intra ocular injections to stabilize retinal detachments. Wong and Thompson, Ophthalmology 95:609–613. Thus the anti thrombosis agents of the invention are extremely safe and nontoxic for patients.

The invention is particularly useful for delivery of nucleotide sequences in the form of gene therapy vectors, or anti-sense of anti-gene type strategies to ultimately alter gene expressions in target cells.

Antisense oligonucleotides represent potential tools in research and therapy by virtue of their ability to specifically inhibit synthesis of target proteins. A major theoretical advantage of these oligos is their potential specificity for binding to one site in the cell. According to one embodiment of the invention a synthetic oligonucleotide of at least 6 nucleotides, preferably complementary to DNA (antigene) or RNA (antisense), which interferes with the process of transcription or translation of endogenous proteins is presented.

Any of the known methods for oligonucleotide synthesis can be used to prepare the oligonucleotides. They are most conveniently prepared using any of the commercially available, automated nucleic acid synthesizers, such as applied biosystems, Inc., DNA synthesizer (Model 380B). According to manufacturers protocols using phosphoroamidite chemistry. After biosystems (Foster City, Calif.). Phosphorothioate oligonucleotides were synthesized and purified according to the methods described in Stek and Zahn J. Chromatography, 326:263–280 and in Applied Biosystems, DNA Synthesizer, User Bulletin, Models 380A-380B-381A-391-EP, December 1989. The oligo is introduced to cells by methods which are known to those of skill in the art. See Iverson, et al., "Anti-Cancer Drug Design", 1991, 6531–6538, incorporated herein by reference.

Traditional limitations of oligonucleotide therapy have been preparation of the oligonucleotide analogue which is substantially resistant to the endo and exonucleases found in the blood and cells of the body. While unmodified oligos have been shown to be effective, several modifications to these oligos has helped alleviate this problem.

Modified or related nucleotides of the present invention can include one or more modifications of the nucleic acid bases, sugar moieties, internucleoside phosphate linkages, or combinations of modifications at these sites. The internucleoside phosphate linkages can be phosphorothioate, phosphoramidate; methylphosphonate, phosphorodithioate and combinations of such similar linkages (to produce mix backbone modified oligonucleotides). Modifications may be internal or at the end(s) of the oligonucleotide molecule and can include additions to the molecule of the internucleoside phosphate linkages, such as cholesterol, diamine compounds with varying numbers of carbon residues between the amino groups, and terminal ribose, deoxyriboase and phosphate modifications which cleave, or crosslink to the opposite chains or to associated enzymes or other proteins which bind to the genome.

These modifications traditionally help shield the oligo from enzymatic degradation within the cell. Any of the above modifications can be used with the method of the invention. However, in preferred embodiment the modification is a phosphorothioate oligonucleotide.

The following examples are for illustration purposes only and are not intended to limit this invention in any way. It will be appreciated by those of skill in the art, that numerous other protein-bioactive agent combinations can be used in the invention and are even contemplated herein. For example, if the filmogenic protein is transferrin, the bioactive agent could be any transferrin binding pharmacologic. In all the following examples, all parts and percentages are by weight unless otherwise mentioned, all dilutions are by volume.

EXAMPLE 1

Phosphorothioate oligonucleotide synthesis

Chain extension syntheses were performed on a 1 $\mu$mole column support on an ABI Model 391 DNA synthesizer (Perkin Elmer, Foster City, Calif.) or provided by Lynx Therapeutics, Inc. (Hayward Calif.). The 1 micromole synthesis employed cyanoethyl phosphoroamidites and sulfurization with tetraethylthiuram disulfide as per ABI user Bulletin 58.

Radiolabeled oligonucleotides were synthesized as hydrogen phosphonate material by Glen Research (Bethesda, Md.). The uniformly $^{35}$S-labeled PS-ODN with sequences 5'-TAT GCT GTG CCG GGG TCT TCG GGC 3' (24-mer complementary to c-myb) (SEQ ID NO:2) and 5' TTAGGG 3' (SEQ ID NO:3) were incubated in a final volume of 0.5 ml with the perfluorocarbon-exposed sonicated dextrose albumin microbubble solution for 30 minutes at 37° C. The solutions were allowed to stand so that the bubbles could rise to the top and 100 microliters were removed from the clear solution at the bottom and 100 microliters were removed from the top containing the microbubbles.

Preparation of Microbubble Agent

Five percent human serum albumin and five percent dextrose were obtained from a commercial source. Three parts of 5% dextrose and one part 5% human serum albumin (total 16 milliliters) were drawn into a 35-milliliter Monojet syringe. Each dextrose albumin sample was hand agitated with 8±2 milliliters of either a fluorocarbon gas (decafluorobutane; molecular weight 238 grams/mole) or 8±2 milliliters of room air, and the sample was then exposed to electromechanical sonication at 20 kilohertz for 80±5 seconds. The mean size of four consecutive samples of the perfluorocarbon-exposed sonicated dextrose albumin (PESDA) microbubbles produced in this manner, as measured with hemocytometry was 4.6±0.4 microns, and mean concentration, as measured by a Coulter counter was 1.4×$10^9$ bubbles/milliliter. The solution of microbubbles was then washed in a 1000 times volume excess of 5% dextrose to remove albumin which was not associated with the microbubbles. The microbubbles were allowed four hours to rise. The lower solution was then removed leaving the washed foam. The washed foam was then mixed with 0.9% sodium chloride.

Binding Assays

The radioactive 24-mer PS-ODN was added to a washed solution of PESDA and room air sonicated dextrose albumin (RA-SDA) microbubbles at a concentration of 5 nM. Non-radioactive PS-ODN 20-mer was added to tubes containing radioactive 24-mer in a series of increasing concentrations (0, 3.3, 10, 32.7, 94.5, 167, and 626 μM). The suspension of bubbles is mixed by inversion and incubated at 37° C. for 60 minutes.

Measurement of Radioactivity

Radioactivity in solutions were determined by liquid scintillation counting in a liquid scintillation counter (model LSC7500; Beckman Instruments GmbH, Munich, Germany). The sample volume was 100 μg to which 5 ml of Hydrocount biodegradable scintillation cocktail was added and mixed. Samples were counted immediately after each experiment and then again 24 hours later in order to reduce the influence of chemiluminescence and of quenching.

Flow cytometry

The uniformity of room air versus perfluorocarbon-containing sonicated dextrose albumin microbubble binding of PS-ODN was determined by flow cytometry. A solution of microbubbles was washed in a 1000 fold excess volume of sterile saline. Three groups of samples were prepared in triplicate as follows; Group A (control) in which 100 μl of microbubbles were added to a 900 μL of saline, Group B in which 100 μ/l of microbubbles were added to 900 μL of saline and 2 μL of FITC-labeled 20-mer was added (final 20-mer concentration is 151 nM), and group C in which 100 μL of microbubbles were added to 800 μL of saline, 2 μL of FITC-labeled 20-mer and 100 μL of unlabeled 20-mer(final concentration is 151 nM). The incubations were all conducted for 20 minutes at room temperature.

Washed microbubble suspensions were diluted in sterile saline (Baxter) and then incubated with FITC-labeled PS-ODN. Flow cytometric analysis was performed using a FACStar Plus (Becton Dickinson) equipped with t 100 mW air-cooled argon laser and the Lysis II acquisition and analysis software. List mode data were employed for a minimum of $10^4$ collected microbubbles and independent analysis a for each sample.

Study Protocol

A variable flow microsphere scanning chamber was developed for the study which is similar to that we have described previously Mor-Avi V., et al "Stability of Albunex microspheres under ultrasonic irradiation; and in vitro study". J Am Soc Echocardiology 7:S29, 1994. This system consists of a circular scanning chamber connected to a Masterflex flow system(Microgon, Inc., Laguna Hills Calif.) The scanning chamber was enclosed on each side by water-filled chambers and bound on each side by acoustically transparent material. The PS-ODN-labeled PESDA microbubbles (0.1 milliliters) were injected as a bolus over one second proximal to the scanning chamber which then flowed through plastic tubing into a tap water-filled scanning chamber at a controlled flow rate of 100 ml/min. As the bubbles passed through the scanning chamber, the scanner (2.0 Megahertz) frequency, 1.2 Megapascals peak negative pressure) was set to either deliver ultrasound at a conventional 30 Hertz frame rate or was shut off. Following passage through the scanning chamber, the solution was then passed through the same size plastic tubing into a graduated cylinder. The first 10 milliliters was discarded. Following this, the next 10 milliliters was allowed to enter into a collection tube. The collection tube containing the effluent microbubbles was allowed to stand in order to separate microbubbles on the top from whatever free oligonucleotide existed in the lower portion of the sample. Drops from both the upper and lower operation of the effluent were then placed upon a hemocytometer slide and analyzed using a 10× magnification. Photographs of these slides were then made and the number of microbubbles over a 36 square centimeter field were then hand-counted. The upper and lower layers of the remaining effluent were then used for analysis of oligonucleotide content using flow cytometry in the same manner described below.

Microbubble samples exposed to the various oligonucleotide solution were mixed 15 (v/v) with a solution of formamide and EDTA and heated to 95° C. for 5 minutes. These samples were then examined on an Applied Biosystems Model 373A DNA sequencer with e 20% polyacrylamide gel. The data were acquired with GeneScanner software so that fluorescence intensity area under the curve could be determined.

EXAMPLE 2

Phosphorothioate Oligonucleotide Binding of PESDA versus RA-SDA Microbubbles The partitioning of PS-ODN to PESDA microbubbles top layer) and non-bubble washed (albumin-free) and unwashed (non-bubble albumin containing) lower layers as counted by liquid scintillation counting are demonstrated in Table 1.

TABLE 1

OLIGONUCLEOTIDES BINDING TO ALBUMIN OF PESDA MICROBUBBLES

| | N | TOP cpm/μl | BOTTOM cpm/μl | RATIO T/B |
|---|---|---|---|---|
| BUBBLES IN THE PRESENCE OF FREE ALBUMIN | | | | |
| TTAGGG | 6 | 125 ± 6.4 | 92.3 ± 6.4 | 1.35 |
| c-myb | 6 | 94.1 ± 17.6 | 77.3 ± 1.2 | 1.35 |
| WASHED BUBBLES (NO FREE ALBUMIN) | | | | |
| TTAGGG | 6 | 210 ± 10.8 | 126 ± 8.7 | 1.67 |
| c-myb | 6 | 200.3 ± 37.4 | 92.7 ± 15.7 | 2.16 |

These data indicate that albumin in the unwashed solution which is not associated with the microbubble will bind to the PS-ODN so that the partitioning of PS-ODN is equivalent between microbubbles(top layer) and the surrounding solution (lower layer; p=HS). Removal of non-microbubble associated albumin (Washed Bubbles in Table 1) does not show a significant partitioning of the PS-ODNs with the PESDA microbubbles (1.67 for TTAGGG PS-ODN and 2.16 for c-myb PS-ODN). The recovery of total radioactivity in the experiments reported in Table 1 is 96% of the radioactivity added which is not significantly different from 100%.

The affinity of binding of PS-ODN to washed microbubbles was evaluated by addition of increasing amounts of excess non-radioactive PS=ODN as a competing ligand for binding sites. In this case a 20mer PS-ODN with sequence 5'-d(CCC TGC TCC CCC CTG GCT CC)-3' (SEQ ID NO:4) was employed to displace the radioactive 24mer. Albumin protein concentrations in the washed microbubble experiments was 0.28±0.04 mg/ml as determined by the Bradford Assay Bradford M et al "A Rapid and Sensitive Method for the quantification of microgram quantities of protein utilizing the principle of protein-dye binding" anal. Bioche,. 72:248, 1976. The observed binding data are presented as a Lineweaver Burke plot in FIG. 1. The equilibrium dissociation constant $K_m$ (calculated for the 7 concentrations which were run in duplicate) for the binding to the microbubbles was $1.76\times10^{-5}$M.

The distribution of FITC-labeled microbubbles is provided in table 2

TABLE 2

DISTRIBUTION OF OLIGONUCLEOTIDE (PS-ODN) BOUND MICROBUBBLES

| | Control PS-ODN | | 151 nM FITC PS-ODN | | Excess unlabeled ODN | |
|---|---|---|---|---|---|---|
| No. | PE | MI | PE | MI | PE | MI |
| 1 | 99.5 | 2.38 | 98.9 | 2109.8 | 97.8 | 1753.1 |
| 2 | 99.3 | 4.07 | 99.1 | 2142.3 | 98.7 | 1710.9 |
| 3 | 99.4 | 3.52 | 99.1 | 2258.5 | 99.3 | 1832.2 |
| mean ± SE | 3.23 ± 0.50 | | 2170 ± 46[1] | | 1765 ± 35[1,2] | |

PE = percent events
MI = mean intensity
SE = standard error
[1]indicates this mean is significantly different form control, $P < 0.001$
[2]indicates this mean is significantly different form 151 nM, $P < 0.001$ The significant decrease in mean fluorescence intensity in the samples containing excess unlabeled PS-ODN indicates the binding to microbubbles is saturable. Consequently, since the binding is saturable, the nonspecific interactions of PS-ODN with the microbubble surface are limited. A Gaussian distribution of PS-ODN to washed PESDA microbubbles indicated that the albumin on these microbubbles had retained its binding site for the oligonucleotide. The absence of a Gaussian distribution for washed RA-SDA indicated loss of albumin binding site 1 for this oligonucleotide occurred during sonication of these microbubbles. For a discussion of albumin binding characteristics particularly as they relate to oligonucleotides see Kumar, Shashi et al "Characterization of Binding Sites, Extent of Binding, and Drug Interactions of Oligonucleotides with Albumin" Antisense Research and Development 5: 131–139 (1995) the disclosure of which is hereby incorporated by reference.

From the foregoing it can be seen that, PS-ODN binds to the albumin in PESDA microbubbles, indicating that the binding site 1 on albumin is biologically active following production of these bubbles by electromechanical sonication. This binding site affinity is lost when the electromechanical sonication is performed only with room sir. Further, removal of albumin not associated with PESDA microbubbles by washing shows a significant partitioning of the PS-ODNs with the microbubbles (Table 1). These observations demonstrate that albumin denaturation does not occur with perfluorocarbon-containing dextrose albumin solutions during sonication as has been suggested with sonication in the presence of air. The retained bioactivity of albumin(especially at site 1) in PESDA microbubbles was confirmed by the affinity of binding of PS-ODN to washed PESDA microbubbles in the presence of increasing amounts of excess non-radioactive PS-ODN as a competing ligand for binding sites (Table 2). The significant decrease in mean fluorescence intensity in the samples containing excess unlabeled PS=-ODN indicates the binding to microbubbles is saturable.

EXAMPLE 3

ALTERED BIODISTRIBUTION VIA MICROBUBBLE DELIVERY OF ANTISENSE OLIGOS

According to the invention antisense phosphorothioate oligonucleotides were designed to the cytochrome P450 IIB1 gene sequence to alter the metabolism of Phenobarbital. The oligonucleotides were conjugated to perfluoropropane exposed sonicated dextrose albumin microbubbles (PESDA) as earlier described and delivered to rats intravenously. The oligonucleotide was synthesized according to the rat cytochrome P450 IIB1 known sequence and had the following sequence: GGAGCAAGATACTGGGCTCCAT (SEQ ID NO:5) AAAGAAGAGAGAGAGCAGGGAG (SEQ ID NO:6)

Male Sprague-Dawley rats (Sasco, Omaha), were used and weighed between 210 to 290 grams for all studies. They were housed in animal quarters at the University of Nebraska Medical Center, AAALAC approved animal resource facility. The animals were exposed to 12 hour light/dark cycle and allowed access to Purina rat chow and tap water ad libitum.

Rats in groups with PB were injected intraperitoneally with phenobarbital (Mallinckrodt, St. Louis) at 80 ml/kg/day×2 days. The PB injections were given simultaneously with the ODN-microbubble injections. Phosphorothioate ODN injections were 1 ml/kg/day×2 days. Sleep times were measured 48 hours after the first injection. The rats were injected intraperitoneally with 100 ml/kg hexobarbital (Sigma, St. Louis), paired fresh daily. The volume of this injection is 1 ml/kg body weight.

Each rat was injected with 100 mg/kg of hexobarbital intraperitoneally. The animals were placed on their backs to insure that they were still under sedation from the hexobarbital. Sleep time is defined as the time they are placed on their backs to the time when they roll over. The sleep times listed are the mean of each animal in the group±standard deviation.

Results indicate that delivery of the oligonucleotide conjugated microbubbles greatly improved efficacy of the drug. Rats given 1/20th dose of oligo experienced a sleep time of more than 50 minutes. This is compared to non microbubble conjugated oligo with an approximate sleep time of 13 minutes Rats were ultimately sacrificed using ethyl ether and microsomes were prepared as described by Franklin and Estabrook (1971). Livers were perfused with 12 ml of 4% saline via the portal vein and then removed from the animal. The livers were minced, homogenized in 0.25M sucrose (Sigma) and centrifuged at 8000×g for 20 minutes at 40° C. in a Sorvall RC2-B centrifuge (Dupont, Wilmington, Del.). The supernatant was saved and resuspended in a 0.25M sucrose and centrifuged at 100,000×g for 45 minutes at 4° C. in a Sorvall OTD55B ultracentrifuge (Dupont). The pellet was resuspended in 1.15% KCL (Sigma) and centrifuged at 100,000×g for 1 hour at 4° C. with the final pellet resuspended in an equal volume buffer (10 mM Tris-acetate, 1 mM EDTA, 20% glycerol; Sigma) and frozen at −80° C.

Protein concentrations were determined by Bradford assay (Bradford, 1976). 80 $\mu$l aliquots of homogenate were added to a 96 well plate (Becton, Dickinson Labware, Lincoln Park, N.J.). 20 $\mu$l of Bradford reagent (Bio-Rad Richmond, Calif.) was then added and the plates read at 595 nm on the microplate reader (Molecular Devices, Newport Minn.). The data was compared to standard curve generated with known concentrations of bovine serum albumin (Sigma).

CYP IIB1 content was determined by pentoxyresorufin O-dealkylation (PROD) activity (Burke et al. 1985). For each microsomal sample, 1 mg protein in 1 ml 0.1M potassium phosphate buffer, 1 ml 2 μM 5-pentoxyresorufin (Pierce, Rockford, Ill.), and 17 μl 60 mM NADPH were mixed and incubated for 10 minutes at 37° C. The mixture was then added to a 2 ml cuvette and read on a RF5000U spectrofluorophotometer (Shimadzu, Columbia, Md.) using an excitation wavelength of 530 nm and emission wavelength of 585 nm. Concentrations of unknowns were calculated from a standard curve of resorufin (Pierce, Rockford, Ill.) standards. Results were recorded in nmol resorufin/mg protein/min.

Direct measurement of CYP IIB1 protein was determined by an ELISA assay using an antibody directed the CYP IIB1 protein (Schuurs and Van Weeman, 1977). 50 μg of liver per well were plated in 100 μl 0.35% sodium bicarbonate buffer overnight on a 96 well nunc-immuno plate (InterMed, Skokie, Ill.). The microsomes were washed 3× with 1% bovine serum albumin in PBS (PBS/BSA) and incubated for 1 hr at 37° C. with 200 μl PBS/BSA. The PBS/BSA was removed and 50 μl of CYP IIB1 antibody (Oxygene, Dallas) was added and incubated for 1 hour at 37° C. The microsomes were washed 5× with saline/tween 20 (Sigma) and had 50 μl horseradish peroxidase antibody (Bio-rad) added. The microsomes were incubated for 1 hour at 37° C., washed 5× with saline/tween 20 and twice with 85% saline. 100 μl of horseradish peroxidase substrate (Kirkegaard & Perry Labs, Gaithersburg, Md.) was added and the plate read continuously in a microplate reader (Molecular Devices) at 405 nm for 1 hour. Results were recorded as horseradish peroxidase activity in mOD/min.

Results demonstrated that the oligo conjugated microbubbles directed the oligo to the liver and kidney. These are site of phenobarbitol metabolism. As described earlier, 100 mg/kg HB was injected i.p. to each animal at the end of 2 days of treatment with PB and/or the ODNs. Control rats had a sleep time of about 23 minutes. PB had a significant reduction in sleep time to about 11.4±4.5 minutes. PB stimulates CYP IIB1 mRNA, as a result, hexobarbital which is hydroxylated by CYP IIB1 is more quickly metabolized and its sedative effect reduced.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

A A C G T T G A G G G G C A T 1 5

( 2 ) INFORMATION FOR SEQ ID NO:2:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:2:

T A T G C T G T G C C G G G G T C T T C G G G C 2 4

( 2 ) INFORMATION FOR SEQ ID NO:3:

( i ) SEQUENCE CHARACTERISTICS:
( A ) LENGTH: 6 base pairs
( B ) TYPE: nucleic acid
( C ) STRANDEDNESS: single
( D ) TOPOLOGY: linear -continued ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:3:

T T A G G G 6

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:4:

C C C T G C T C C C C C C T G G C T C C 2 0

( 2 ) INFORMATION FOR SEQ ID NO:5:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:5:

G G A G C A A G A T A C T G G G C T C C A T 2 2

( 2 ) INFORMATION FOR SEQ ID NO:6:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:6:

A A A G A A G A G A G A G A G C A G G G A G 2 2

What is claimed is:

1. A method for delivering a biological agent to specific tissue sites comprising:

forming a solution of a plurality of albumin encapsulated, insoluble gas-filled microbubbles, said microbubbles associated to said biological agent;

administering said solution to an animal; so that said protein directs the microbubble-associated agent to sites of bioprocessing of said protein and upon dissipation of the microbubble releases said agent;

wherein said biological agent is selected from the group consisting of naproxen, piroxicam, warfarin, furosemide, phenylbutazone, valproic acid, sulfisoxazole, ceftriaxone, and miconazole.

2. The method of claim 1 wherein said insoluble gas is selected from the group consisting of perfluoromethane, perfluoroethane, perfluoropropane, perfluorobutane, and perfluoropentane.

3. The method of claim 2 wherein said gas is perfluoropropane.

4. The method of claim 1 wherein said microbubbles are formed by the steps of:

mixing an aqueous solution comprising about 2% to about 10% by weight of human serum albumin diluted about two-fold to about eight-fold with 5% to 50% by weight of dextrose; and exposing said solution to a sonication horn to create cavitation at particulate sites in said solution thereby generating stable microbubbles from about 0.1 to 10 microns in diameter.

5. The method of claim 4 wherein said dilution of albumin with dextrose is a three-fold dilution.

6. The method of claim 4 wherein said human serum albumin is a 5% by weight solution.

7. The method of claim 4 wherein said dextrose is a 5% by weight solution.

8. A composition for delivery of a biological agent to a target site comprising:

an aqueous suspension comprising a plurality of albumin encapsulated insoluble gas-filled microbubbles and;

a biological agent selected from the group consisting of naproxen, piroxicam, warfarin, furosemide, phenylbutazone, valproic acid, sulfisoxazole, ceftriaxone, and miconazole associated to said albumin.

9. The composition of claim 8 wherein said gas is a perfluorocarbon gas.

10. The composition of claim 8 wherein said gas is selected from the group consisting of perfluoromethane, perfluoroethane, perfluoropropane, perfluorobutane, and perfluoropentane.

11. The composition of claim 10 wherein said gas is perfluorobutane.

12. The composition of claim 10 wherein said gas is perfluoropropane.

13. The composition of claim 8 wherein said microbubbles are 0.1 to 10 microns in diameter.

14. The method of claim 1 wherein said target site is the liver and the kidney of said animal.

* * * * *